(12) United States Patent
Adler

(10) Patent No.: US 6,571,804 B2
(45) Date of Patent: Jun. 3, 2003

(54) DENTAL FLOSS APPLICATOR

(76) Inventor: Harold A. Adler, 3909 Dalehurst Dr., Bakersfield, CA (US) 93306

( * ) Notice: Subject to any disclaimer, the term of this patent is extended or adjusted under 35 U.S.C. 154(b) by 28 days.

(21) Appl. No.: 09/927,709

(22) Filed: Aug. 11, 2001

(65) Prior Publication Data

US 2003/0029472 A1 Feb. 13, 2003

(51) Int. Cl.[7] .............................................. A61C 15/00
(52) U.S. Cl. ..................................... 132/325; 132/328
(58) Field of Search ................................ 132/309, 311, 132/323, 324, 325, 328; 401/191

(56) References Cited

U.S. PATENT DOCUMENTS

| | | | |
|---|---|---|---|
| 664,126 A | | 12/1900 | Cowan ........................ 132/325 |
| 677,947 A | | 7/1901 | Cowan ........................ 132/324 |
| 1,507,313 A | | 9/1924 | Hudson ........................ 132/326 |
| 1,882,204 A | | 10/1932 | Zrna ........................... 132/323 |
| 2,067,889 A | * | 1/1937 | Collingbourne ............. 132/324 |
| 2,510,194 A | * | 6/1950 | Thomas ....................... 132/325 |
| 5,139,038 A | * | 8/1992 | El Gazayerli ............... 132/325 |
| 5,423,427 A | * | 6/1995 | Brown ......................... 132/311 |
| 5,735,298 A | * | 4/1998 | Mayne et al. ............... 132/309 |
| 5,860,435 A | * | 1/1999 | Hippensteel ................ 132/325 |

* cited by examiner

Primary Examiner—John J. Wilson
(74) Attorney, Agent, or Firm—Kelly Bauersfeld; Lowry & Kelley, LLP

(57) ABSTRACT

An improved dental floss applicator is provided in the form of a compact case for receiving and storing a spool of dental floss together with an applicator fork for use in manipulating a length of dental floss for cleaning a person's teeth. The applicator fork is pivotally mounted to the case for movement between a normal stored position within the hollow interior of the case, and a deployed position extending outwardly from the case for use. In the stored position, the spool of dental floss is nested within the fork to provide a compact overall geometry. A lock tab on the case engages mating recessed seats on the fork for securely retaining the fork relative to the case in each of its stored and deployed positions.

25 Claims, 3 Drawing Sheets

DENTAL FLOSS APPLICATOR

BACKGROUND OF THE INVENTION

This invention relates generally to devices for storing and manipulating dental floss used for cleaning a person's teeth. More particularly, this invention relates to an improved dental floss applicator of the type including an applicator fork, wherein the applicator fork is carried within a compact case together with a spool of dental floss and adapted for quick and easy deployment for use.

Dental floss is widely recognized as an important and effective tool for maintaining a high level of dental hygiene. In this regard, modern dental floss comprises a length of relatively strong fiber-based thread or filament for manipulation into the space between adjacent teeth for effectively dislodging and removing plaque build-up and trapped food particles and the like. The dental floss is typically provided on a spool from which a selected length is cut for use. In the most common form, the floss spool is contained within a compact housing or case of molded plastic or the like to include an outlet port through which the floss can be manually drawn and then severed by pulling the floss past a relatively sharp-edged metal cutter element. Many dental professionals recommend that patients employ dental floss to clean their teeth on a daily basis, and preferably after each meal in conjunction with traditional brushing of the teeth.

Manipulation of the flexible dental floss with the hands and fingers can be a difficult procedure for many people. As a result, a variety of dental floss applicators have been developed over the years in an effort to facilitate handling of the dental floss during teeth cleaning. Such floss applicators have generally comprised a fork-shaped element with a pair of spaced-apart tines or arms through which a length of dental floss is threaded and retained. The fork element is designed for holding the segment of the dental floss in a relatively taut condition for ease of handling and orientation to manipulate the floss segment between an adjacent pair of teeth. See for example, U.S. Pat. Nos. 664,126; 677,947; 1,507,313 and 1,882,204. In some designs, the fork element is mounted onto a housing or case containing a spool of the dental floss, and the fork element may be adapted for movement to a stored position within or overlying the case when not in use. However, the overall size and shape of such dental floss applicators, particularly with the fork element in a stored position, has not been sufficiently compact to provide the requisite inducement for many persons to carry and use such applicators on a regular basis. Moreover, in a deployed state, the fork has typically been supported by the case in a somewhat loose or nonrigid fashion wherein a degree of movement between the fork and case can make it difficult to manipulate the fork and floss to clean teeth. In addition, in a common configuration, the fork comprises an elongated structure adapted to support the floss extending perpendicular to a pivot axis of the fork structure so as to facilitate flossing of front teeth with a sawing type action. Unfortunately, this geometry results in a structure wherein effective floss access to the rear teeth is awkward and difficult, requiring the use of one hand to pull the cheek away from the teeth and gums.

There exists, therefore, a need for further improvements in and to dental floss applicators of the type having a deployable applicator fork adapted for storage together with a spool of dental floss within a highly compact case. The present invention fulfills this need and provides further related advantages.

SUMMARY OF THE INVENTION

In accordance with the invention, an improved dental floss applicator comprises a compact hollow case for receiving and supporting a spool of dental floss together with a generally Y-shaped applicator fork. The applicator fork is pivotally mounted to the case for movement between a normal stored position therein, and a deployed position projecting outwardly from the case for use. In the stored position, the floss spool is retained in a position nested within the applicator fork, to provide a highly compact overall size and shape. In the deployed position, the case interlocks with the applicator fork at multiple contact points for secure and stable support thereof, whereby the case provides a sturdy handle structure for manipulating the applicator fork during cleaning of the teeth.

In the preferred form of the invention, the hollow case is formed from lightweight unitary or one-piece molded plastic or the like to define a generally shell-shaped pair of matingly interfitting first and second case members interconnected along adjacent side edges by one or more living hinges. Latch members are provided along opposite side edges of the case members for releasable snap-fit retention thereof in a closed position. Mounting posts project upwardly within the first case member for snap-fit engagement with one or more pivot pins formed on a base of the applicator fork, wherein the fork base supports a pair of diverging tines or arms having distal end tips shaped for releasable snap-fit and draw-through reception of the dental floss. The applicator fork may also be formed from molded plastic and is pivotally supported by the mounting posts for swinging movement about a pivot axis between a stored position within the case when said case members are closed, and a deployed position with the fork arms projecting outwardly from the case wherein said case members can also be closed. One or more flaps are desirably formed in opposing relation on the case members and coupled thereto by living hinges to accommodate outward projection of the applicator fork in the deployed position with the case members closed. Importantly, in the stored position, the floss spool is positioned within the case in nested relation between the fork arms to achieve a highly compact configuration. In the deployed position, the fork arms support a length of floss to extend generally parallel to the fork pivot axis for facilitated floss access to front as well as rear teeth.

A lock tab is formed on the second case member for engaging the applicator fork to retain said fork is a secure and stable manner relative to the closed case. The lock tab is received into a recessed seat formed in the fork base when the applicator fork is in the deployed position and the case is closed, whereby the applicator fork is rigidly interconnected and locked with respect to the case. The lock tab cooperates with the mounting posts and the edges of the case members adjacent the flaps to retain the fork at multiple contact points, so that said case can be used as a sturdy handle during manipulation of the fork to clean a person's teeth. In the preferred form, the lock tab is also received into a recessed seat in the fork base in the stored position for securely stowing the applicator fork within the case when not in use. Floss cutter and tie-down elements may also be included on the applicator fork.

Other features and advantages of the present invention will become more apparent from the following detailed description taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
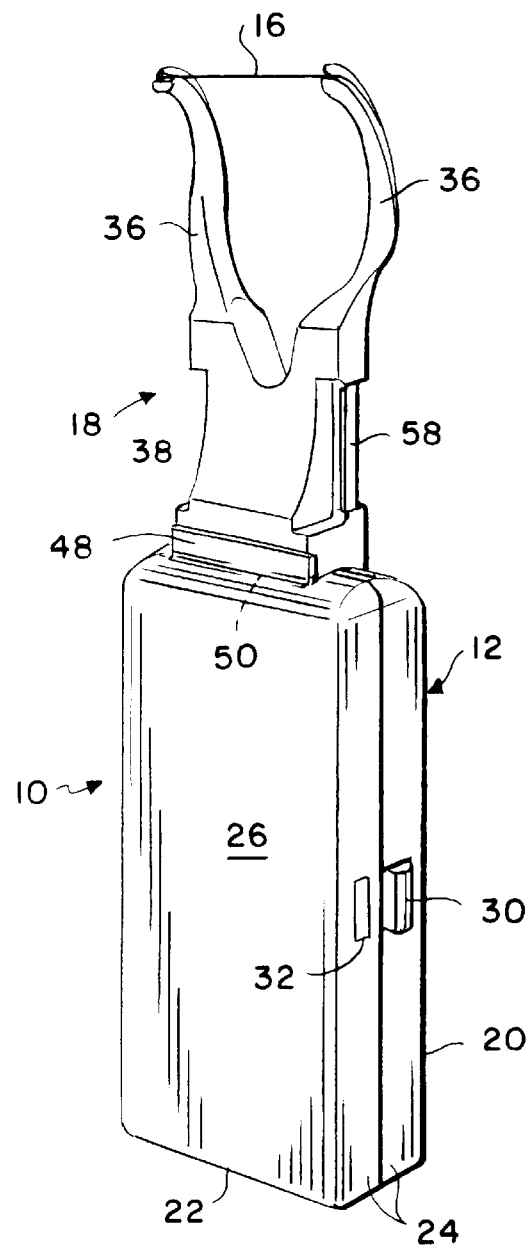
FIG. 1 is a front side perspective view depicting a dental floss applicator embodying the novel features of the invention.

As shown in the exemplary drawings, an improved dental floss applicator referred to generally by the reference numeral 10 comprises a compact case 12 for receiving and supporting a spool 14 of dental floss 16, together with an applicator fork 18 for facilitated manipulation of the floss 16 to clean a person's teeth. The applicator fork 18 is mounted within the case 12 for swinging movement about a pivot axis between a stored position (FIGS. 3 and 7) contained compactly within the case and having the floss spool 14 nested therein, and a deployed position (FIGS. 1 and 2) extending outwardly from the case for use.

Figure 3:
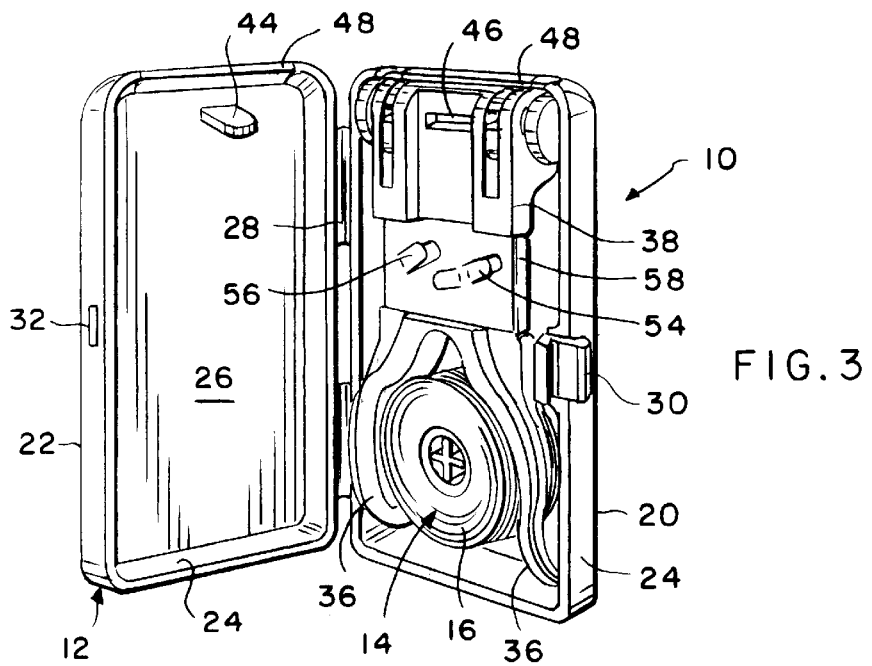
FIG. 3 is a perspective view showing the dental floss applicator of FIGS. 1 and 2, but illustrating an applicator fork in a stored position within an open case.
Figure 4:
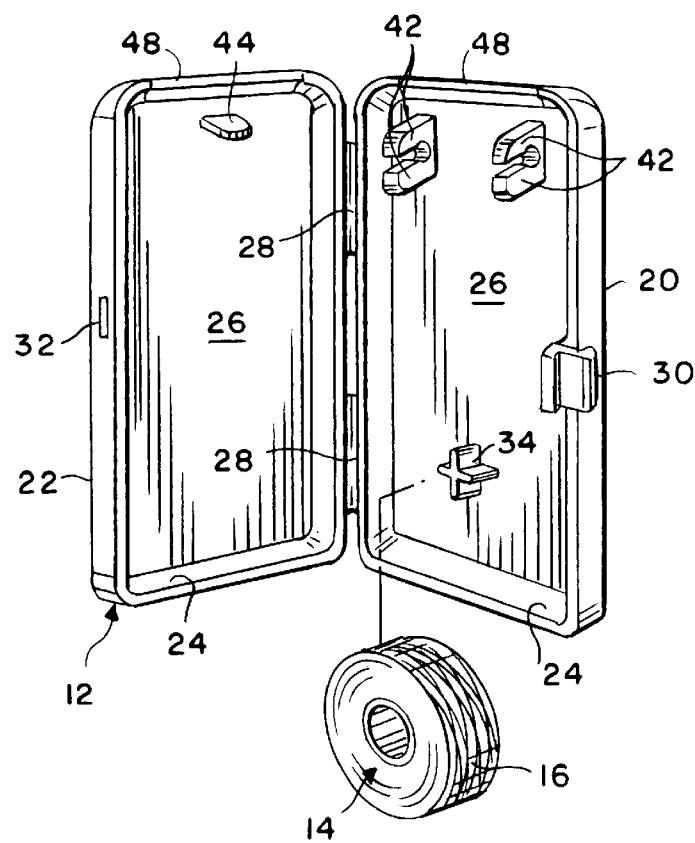
FIG. 4 is a perspective view similar to FIG. 3, but depicting the open case with the applicator fork removed and a floss spool shown in exploded relation.

The case 12 of the dental floss applicator 10 is conveniently and economically constructed from a lightweight and preferably unitary plastic molding to include first and second matingly interfitting case members 20 and 22 each having a generally shell-shaped construction to include a peripheral edge wall 24 bounding a generally planar rectangular panel 26. These case members 20, 22 are shown with their edge walls 24 joined along an adjacent side by a pair of hinges 28 which in the preferred embodiment comprise living hinges. A latch clip 30 is formed on the opposite side of the first case member 20 for releasable but secure snap fit reception into and engagement with a latch slot 32 formed on the opposite side of the second case member 22, for releasibly retaining the two case members 20, 22 in a closed condition. Alternately, it will be understood that the latch slot 32 may comprise an undercut notch formed in the edge wall 24 of the second case member 22. In either construction, the latch clip 30 may be depressed to release the clip from the second case member 22 and permit the case 12 to be opened as viewed in FIGS. 3, 4 and 6.

The spool 14 of dental floss 16 is contained within the case 12, generally within a lower region thereof as by rotatably locating the spool 14 on a short hub 34 (FIG. 4) shown with a generally X-shaped and preferably tapering profile protruding inwardly from the panel 26 of the first case member 20. This hub 34 loosely supports the spool 14 in a manner permitting the floss 16 to be unwound therefrom on an as-needed basis, as will be described in more detail. When the case 12 is closed, the spool 14 is rotatably retained between the two case members 20, 22.

Figure 5:
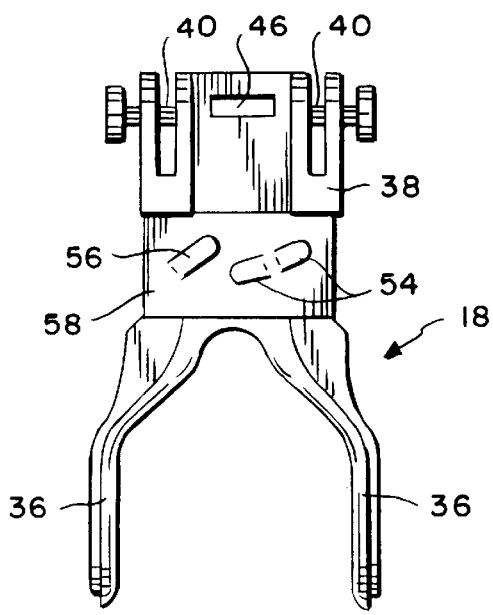
FIG. 5 is a rear side elevation view of the applicator fork.

The applicator fork 18 is also adapted for mounting within the case 12. More specifically, as shown best in FIGS. 3, 5 and 6, the applicator fork 18 comprises a pair of spaced-apart fork arms or tines 36 diverging in a generally Y-shaped configuration from a base 38, wherein the base 38 and fork arms 36 may also be constructed from a lightweight and preferably unitary plastic molding. The base 38 in turn includes a pair of coaxial pivot pins 40 (FIG. 5) for snap-fit engagement respectively with pairs of mounting posts 42 formed to project inwardly from the panel 26 of the first case member 20, within an upper region of the case. The pivot pins 40 enable the applicator fork 18 to be pivotally moved relative to the case member 20 about a pivot axis defined by the pivot pins 40 to a normal stored position lying substantially flat within said first case member 20 and with the floss spool 14 nested substantially planar between the fork arms 36 to provide an extremely compact product profile. In this stored position, the two case members 20, 22 can be closed and latched with the fork 18 and spool 14 concealed and stored therein, as viewed in FIG. 7, and with the fork arms 36 lying closely on opposite sides of the spool to provide a highly compact configuration. A lock tab 44 formed to project inwardly from the panel 26 of the second case member 22 conveniently seats within a lock recess 46 formed in the fork base 38, when the case members are closed, to retain the applicator fork 18 in the stored position.

Figure 6:
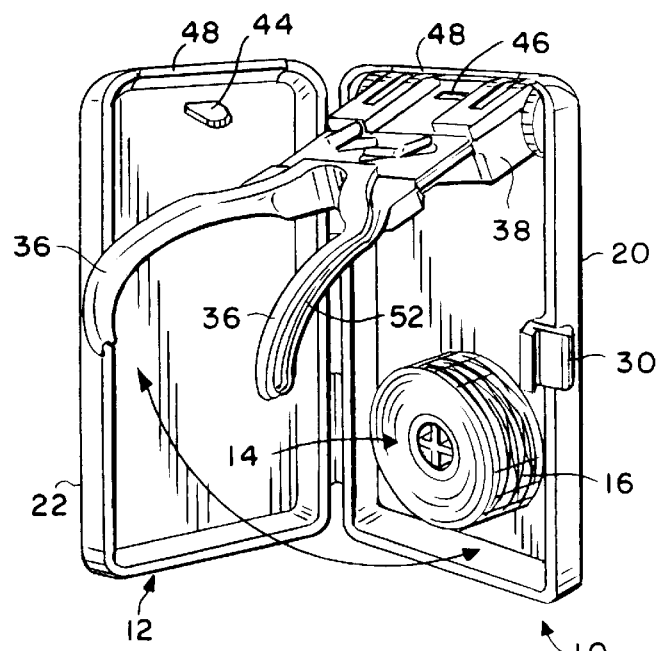
FIG. 6 is a perspective view similar to FIG. 3, and showing swinging movement of the applicator fork between a stored position and a deployed position.
Figure 7:
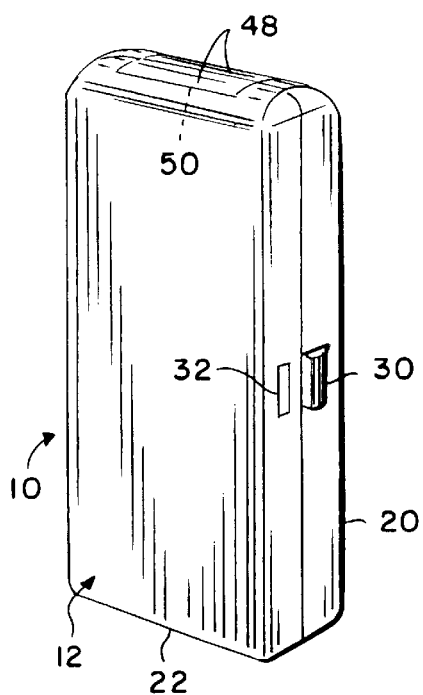
FIG. 7 is a perspective view showing the case in a closed position with the applicator fork stored therein.

The pivot pins 40 on the applicator fork 18 also enable the fork to be pivotally moved, when the case members are opened, from the stored position to a deployed position extending outwardly from the case 12, whereupon the case can be reclosed to provide a convenient and sturdy handle for manipulating the fork to clean a person's teeth. FIG. 6 shows the case members 20, 22 in an open position to permit swinging displacement of the applicator fork 18 between the stored and deployed positions. In the deployed position, the fork base 38 protrudes outwardly from an upper edge of the case members through a port defined by an adjacent pair of flaps 48 formed in the edge walls 24 of the two case members to accommodate the fork. These flaps 48 are respectively joined to the associated case member by living hinges 50 (FIGS. 1 and 2) which cause the flaps to return to normal positions closing the fork port when the applicator fork 18 is in the stored position as depicted in FIG. 7, thereby minimizing or eliminating entry of dirt and other contaminants into the interior of the case 12.

In accordance with one aspect of the invention, the lock tab 44 on the second case member 22 also extends into the lock recess 46 formed in the fork base 38 when the applicator fork 18 is in the deployed position with the case members 20, 22 closed. With this construction, the lock tab 44 securely anchors the applicator fork 18 to provide a substantially rigid and interlocked connection therebetween. In this regard, the case members 20, 22 are sufficiently rigid in the regions of the flaps 48 to clamp against and retain the fork 18 in a secure and rigid manner. The lock tab 44 thus cooperates with the edges of the case members 20, 22 and the mounting ports 42 to provide a multiple three-point contact support to rigidly retain the fork 18 in the deployed position. Accordingly, during use of the fork 18 in a teeth cleaning procedure, the closed case members 20, 22 provide an easily grasped handle for use in holding and manipulating the floss applicator 10, substantially without any significant movement or bending between the fork 18 and the case 12.

Figure 2:
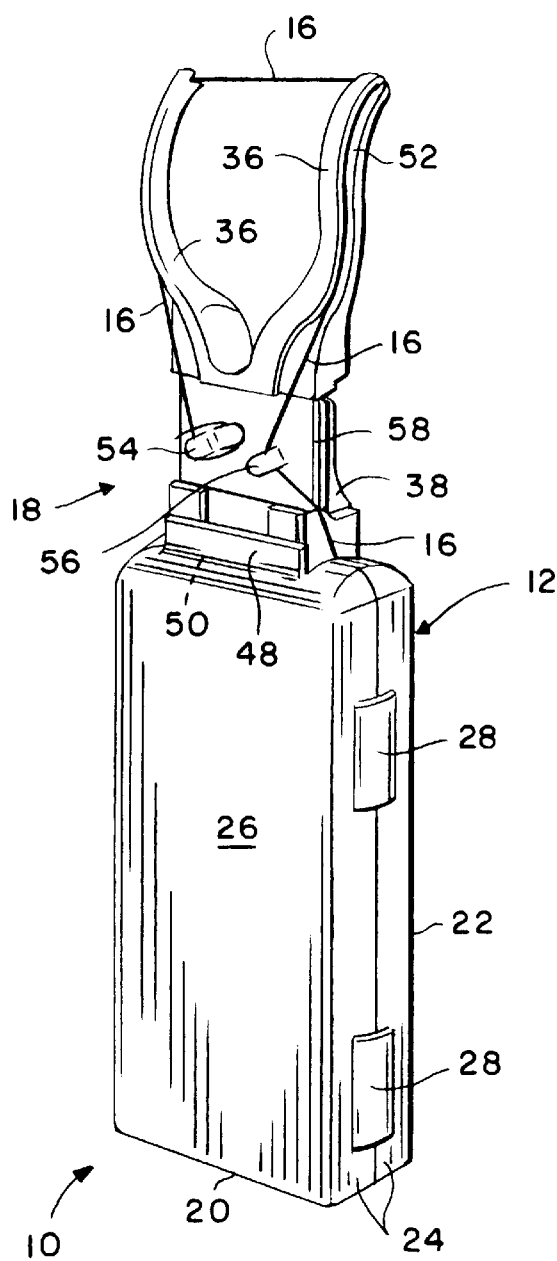
FIG. 2 is a rear side perspective view of the dental floss applicator of FIG. 1.

In use, a length of the dental floss 16 is drawn from the spool 14 and appropriately threaded over the ends of the fork arms 36, as viewed in FIGS. 1 and 2, with the segment spanning the fork arms extending generally parallel to the pivot axis defined by the pivot pins 40. This geometry has been found to greatly facilitate use of the device in flossing front teeth as well as rear teeth, particularly without requiring the cheek to be pulled back and held in order to access the rear teeth. To support the floss, the fork arms 36 may be formed with channels 52 formed in the outboard side edges thereof for guided reception of the floss 16 to the distal end tips of the forks, wherein these tips can be shaped as by pinching together the opposite sides of the channels 52 for snap-fit and slide-through reception of the floss. The dental floss 16 can thus be looped over the fork arms 36 to span therebetween as shown in FIGS. 1 and 2, and then looped back toward the base 38 where the floss can be anchored by wrapping about retention or tie-down elements 54 and severed by a cutter element 56. In the preferred form, the retention elements 54 and the cutter element 56 are formed as short tabs struck upwardly from a relatively thin metal plate 58 adapted for snap-fit mounting onto the fork base 38.

The dental floss applicator 10 of the present invention thus provides a compact and self-contained package for the floss spool 14 and the applicator fork 18. The package is quickly and easily manipulated to move the applicator fork 18 from the stored position to the deployed position for use, with the case 12 being re-closed to provide a sturdy supporting handle facilitating a teeth cleaning procedure.

A variety of further modifications and improvements in and to the dental floss applicator 10 of the present invention will be apparent to those skilled in the art. Accordingly, no limitation on the invention is intended by way of the foregoing description and accompanying drawings, except as set forth in the appended claims.

What is claimed is:

1. A dental floss applicator, comprising:
   a case including a pair of hingedly coupled case members movable between an open position and a closed position, said case members defining a hollow interior for said case in said closed position;
   a supply of dental floss within said case, said supply comprising a spool of dental floss supported by said case; and
   an applicator fork mounted on said case for swinging movement between a stored position within said case and a deployed position extending outwardly from said case, said applicator fork having a pair of spaced-apart fork arms adapted to support a length of said dental floss spanning therebetween, said supply of dental floss being nested generally between said fork arms when said applicator fork is in said stored position.

2. The dental floss applicator of claim 1 wherein said case members are movable to said closed position with said applicator fork in said deployed position, and further including lock means on said case for engaging said applicator fork in said deployed position when said case members are in said closed position for securely supporting said applicator fork relative to said case.

3. The dental floss applicator of claim 2 wherein said applicator fork is pivotally mounted to one of said case members, and wherein said lock means comprises a lock tab formed on the other of said case members for engagement with a recessed seat formed on said applicator fork.

4. The dental floss applicator of claim 3 wherein said case members cooperatively define an opening through which said applicator fork extends in said deployed position, at least one of said case members defining a substantially rigid edge for engaging and supporting said applicator fork in said deployed position.

5. The dental floss applicator of claim 1 further including means for rotatably supporting said floss spool within said case.

6. The dental floss applicator of claim 1 wherein said length of dental floss spanning between said fork arms is supported to extend generally in parallel with a pivot axis for swinging movement of said applicator fork between said stored and deployed position.

7. The dental floss applicator of claim 1 wherein said case members are formed from molded plastic and hingedly interconnected by at least one living hinge.

8. The dental floss applicator of claim 1 further including latch means for releasibly retaining said case members in said closed position.

9. The dental floss applicator of claim 1 wherein said applicator fork is formed from molded plastic.

10. The dental floss applicator of claim 1 wherein said applicator fork is pivotally mounted to one of said case members, and further including a lock tab formed on the other of said case members for engagement with a recessed seat formed on said applicator fork for securely retaining said applicator fork relative to said case with said applicator fork in each of said stored and deployed positions when said case members are in said closed position.

11. The dental floss applicator of claim 1 further including a cutter element mounted on said applicator fork for severing the dental floss.

12. The dental floss applicator of claim 1 further including a tie-down element mounted on said applicator fork for retaining the dental floss.

13. A dental floss applicator, comprising:
   a case including a pair of hingedly coupled case members movable between an open position and a closed position, said case members defining a hollow interior for said case in said closed position;
   a supply of dental floss within said case; and
   an applicator fork mounted on said case for swinging movement between a stored position within said case and a deployed position extending outwardly from said case, said applicator fork having a pair of spaced-apart fork arms adapted to support a length of said dental floss spanning therebetween, said supply of dental floss being nested generally between said fork arms when said applicator fork is in said stored position;
   said case including at least one flap for normally closing one end of said case when said applicator fork is in said stored position, said at least one flap being movable to accommodate said applicator fork in said deployed position extending outwardly from said case when said case members are in said closed position.

14. The dental floss applicator of claim 13 wherein said at least one flap comprises a pair of flaps formed respectively on said case members in opposing relation to each other.

15. The dental floss applicator of claim 14 wherein said case members are formed from molded plastic, and further wherein said flaps are respectively joined to said case members by living hinges.

16. A dental floss applicator, comprising:
   a compact hollow case including a pair of interfitting case members hingedly joined along adjacent side edges for movement between an open position and a closed position, and latch means on opposite side edges of said case members for releasibly retaining said case members in said closed position;
   a spool of dental floss rotatably carried within said case; and
   an applicator fork having a fork base pivotally mounted to one of said case members for swinging movement about a pivot axis between a stored position disposed substantially within said case and permitting movement of said case members to said closed position, and a deployed position extending outwardly from said case and permitting movement of said case members to said closed position, said applicator fork being movable between said stored and deployed positions when said case members are in said open position;

said applicator fork further including a pair of spaced-apart fork arms extending from said fork base adapted to support a length of dental floss spanning therebetween and disposed generally parallel to said pivot axis, said fork arms being positioned within said case with said spool nested therebetween when said applicator fork is in said stored position.

17. The dental floss applicator of claim 16 further including lock means on said case for engaging said applicator fork in said deployed position when said case members are in said closed position for securely supporting said applicator fork relative to said case.

18. The dental floss applicator of claim 17 wherein said lock means comprises a lock tab on one of said case members for engaging a recessed seat formed in said fork base.

19. The dental floss applicator of claim 18 wherein said case members cooperatively define an opening through which said applicator fork extends in said deployed position, at least one of said case members defining a substantially rigid edge for engaging and supporting said applicator fork in said deployed position.

20. The dental floss applicator of claim 16 wherein said case members are formed from molded plastic and hingedly interconnected by at least one living hinge.

21. The dental floss applicator of claim 16 further including a cutter element mounted on said fork base for severing the dental floss.

22. The dental floss applicator of claim 16 further including a tie-down element mounted on said fork base for retaining the dental floss.

23. The dental floss applicator of claim 16 wherein said case includes at least one flap for normally closing one end of said case when said applicator fork is in said stored position, said at least one flap being movable to accommodate said applicator fork in said deployed position extending outwardly from said case when said case members are in said closed position.

24. The dental floss applicator of claim 23 wherein said at least one flap comprises a pair of flaps formed respectively on said case members in opposing relation to each other.

25. The dental floss applicator of claim 24 wherein said case members are formed from molded plastic, and further wherein said flaps are respectively joined to said case members by living hinges.

* * * * *